United States Patent [19]

Ma

[11] Patent Number: 5,792,933
[45] Date of Patent: Aug. 11, 1998

[54] FIBER-SPECIFIC PROTEIN EXPRESSION IN THE COTTON PLANT

[75] Inventor: Din-Pow Ma, Mississippi State, Miss.

[73] Assignee: Mississippi State University, Mississippi State, Miss.

[21] Appl. No.: 539,304

[22] Filed: Oct. 4, 1995

[51] Int. Cl.[6] ................ C12N 15/00; C12N 15/63; C07H 21/04; C12P 21/06
[52] U.S. Cl. ............... 800/205; 800/255; 800/DIG. 27; 435/69.1; 435/172.3; 435/320.1; 536/24.1; 536/23.6
[58] Field of Search ................ 800/205, 255, 800/DIG. 27; 435/69.1, 172.3, 320.1; 536/34.1, 23.6

[56] References Cited

U.S. PATENT DOCUMENTS

| | | | |
|---|---|---|---|
| 5,495,070 | 2/1996 | John | 800/205 |
| 5,521,078 | 5/1996 | John | 435/172.3 |

*Primary Examiner*—Douglas W. Robinson
*Assistant Examiner*—Thanda Wai
*Attorney, Agent, or Firm*—Oblon, Spivak, McClelland, Maier & Neustadt, P.C.

[57] ABSTRACT

A cotton fiber-specific lipid transfer protein, its amino acid sequence, its protein-encoding DNA sequence, and its 5' flanking sequence are disclosed. In addition, the promoter and upstream sequences of two other lipid transfer proteins are disclosed. Finally, methods for utilizing these sequences to express genes of interest in *Gossypium hirsutum* L., in a fiber-specific fashion, are described.

6 Claims, 9 Drawing Sheets

```
GACGACAATCACCAATAGTTCTACTACTCCAAGCAAGTATTTTCCTTAGACGTTTGTTTT      60

TCTTGTGATTAATCGATATGGCTAGCTCAATGTCCCTTAAACTTGCATGTGTGGTGGTGT     120
                M  A  S  S  M  S  L  K  L  A  C  V  V  V        14

TGTGCATGGTAGTGGGTGCACCCCTGGCTCAAGGGGCCGTAACCTCTGGTCAAGTCACAA     180
 L  C  M  V  V  G  A  P  L  A  Q  G  A  V  T  S  G  Q  V  T      34

ACTCCCTCGCACCCTGCATTAATTACTTGAGAGGCAGTGGTGCTGGTGCCGTTCCCCCAG     240
 N  S  L  A  P  C  I  N  Y  L  R  G  S  G  A  G  A  V  P  P      54

GTTGCTGCACGGGCATCAAATCTCTCAACTCCGCCGCCCAAACAACACCAGTCCGGCAAG     300
 G  C  C  T  G  I  K  S  L  N  S  A  A  Q  T  T  P  V  R  Q      74

CAGCTTGCAGATGCATCAAAAGTGCGGCCGCCGGCATTACTGGCATCAACTTTGGCCTTG     360
 A  A  C  R  C  I  K  S  A  A  A  G  I  T  G  I  N  F  G  L      94

CAAGCGGACTCCCAGGCAAGTGCGGTGTCAACATCCCTTACAAGATCAGCCCTAGCACTG     420
 A  S  G  L  P  G  K  C  G  V  N  I  P  Y  K  I  S  P  S  T     114

ACTGCAACAGCGTCAAGTGAAGTTTTGGCATGGAAAGTTCACCAGCTAGTGGAAGCCAAA     480
 D  C  N  S  V  K  *                                            120

ATAACGATAGCTACAGAATAAATATGGATGTTAAAATTCCAGAGTTATGCGTTGTGTACT     540

ATGCCGCTTTATGCGACTACGTAATATAATCTTTATCTACAAATTAGTATCAAAAAAAAA     600

AAAAAAAAA                                                        609
```

FIG.1

```
  1  GAA TTC CCC TTC TGT TTT AGT TGT CTT TCT TCA TCT TTT CCC TTT TCT            48

49  GCA AGC ATG CAA TTG TGT TGT ACG GTA AGT TTC TGT TTT ATT AAA CTT            96

97  AAA TGT TAC TCT GGA TAA GGG ATT AAG GGG TGT TTT GTT GAC TGT TTA           144

145  GGA GTC GAT CGT GAG GCT GGA ATT AAC GTT CAT CTA TTT GAC TCG AAG           192

193  TGG TGA TCG TTT GGT AAG TGT ACA AGG TAT GCG TTT CTA TGT GTT GGG           240

241  CGA GTG GTT TGG CAT TGA ATT AGG GCA ACT AAC AGG CAC CAA TGC CTA           288

289  ACC AAG TTG TAT TCG TAC GCC TTT CTT AGT TTT TTT TTC CAT ATT CCT           336

337  TCA CTC AAC TTT TGT CTA TAA AAA CCC TCC AAC CAG CAA TCC CAT TAC           384

385  TAA TAC TCC AAC CAC TTT CTT ACA AGT TGG TAA AAT TAT TAG TTT TTC           432

433  TTG TAA TTA ATC GAT ATG GCT AGG TCA ATG TCT CTT AAG CTT GCA TGT           480
  1                      M   A   R   S   M   S   L   K   L   A   C            11

481  GTA GTG GTG TTG TGC TTG TTG GTG GAT GCA CCC CTG GCT CAA GGG GCC           528
 12    V   V   V   L   C   L   L   V   D   A   P   L   A   Q   G   A           27

529  ATA AGC TAT GAT CAA GTC AAA TCC TCC CTC CTA CCC TGC GTT GGT TAC           576
 28    I   S   Y   D   Q   V   K   S   S   L   L   P   C   V   G   Y           43
```

FIG.2A

```
577  GTG AGA GGT AAT AAT GCT CGT CCT GCT CCC CCA AAT TAC TGT AAA GGC   624
 44   V   R   G   N   N   A   R   P   A   P   P   N   Y   C   K   G    59

625  ATC AGA TCT CTC AAA TCT GCC GCC CGA ATA AGA CTA GAT CGG CAA GCA   672
 60   I   R   S   L   K   S   A   A   R   I   R   L   D   R   Q   A    75

673  GCT TGT AAA TGC ATC AAA AGT CTG GCC GCC GAC ATT TCT GAC ATC AAC   720
 76   A   C   K   C   I   K   S   L   A   A   D   I   S   D   I   N    91

721  TAT GGC GTT GCA GCC GGA CTC CCA GGC CAG TGC AAC GTC CAC ATC CCT   768
 92   Y   G   V   A   A   G   L   P   G   Q   C   N   V   H   I   P   107

├──────→ intron
769  TAC AAG ATC AGC CCT AGC ATT GAC TGC AAA AGG TTC GTA TCT AAT TTA   816
108   Y   K   I   S   P   S   I   D   C   K   R                       118

817  AGC TAG ACT TCA TTG AAA TTA CGA AAA AGA AAA TGG CCC CAA ATT TGT   864

865  TGC ATA ACA TTA AGT GAG TTT ATT GAT TAA TTA ATT GAT GAA TGT TTT   912

←──────┤
913  ACT TTG GTG TGG TTG CAT TTG CAG AGT CAA GTG ACG TGT GGC CAT GGA   960
                                       V   K   *                     121

961  AGT TGG GAT CAG CTA ATG GAA GGG AAA TGG TGG TGT ACT CAC TAA AAA  1008

1009 TTA TCC TAG TTT TAG AGT TGG TGA CGA TGT ACA AGG TCG ATT TAT GCG  1056

1057 ACT ATC TAA TAA TAT CTT TAC CTA CTC AAA ATA TTA ATA TCA CTC TCA  1104
```

FIG.2B

```
1105  ATG GTT GTT TCT TCT ATG TAT ACA CTC TTC ATT TCC CTT TGC TTT GTT        1152

1153  TTT TTT TCC AAG TCA AGC GTA CCA TTT CAA GCA TTT CAT ATA AAC ACC        1200

1201  CGC GTG TCC TAA TGA TAA TGG AAA CCC ACG TGA GCC AGA TAT GGA TGC        1248

1249  TCA ATT ATT CGA AGA TGA ATG TAT GGA CCA GCA TTT TTA AGC AAT AAG        1296

1297  AAT AAA TAA ATA AAA ATT TCA AGT CAA TTG AAT ACA AAT CTT AAA TCC        1344

1345  TAC GAT GAA TGA ATA CAT CAT TTA AAT TTA AAA CAA AAA AAT TAT TTA        1392

1393  AAT AAT TTC TTT TTT TAA TTT TTT TAG TTG CTC AAA TGT GAA TTA TGA        1440

1441  ATA GGT CTA AGA GTA TTG TTG AGC CAA GTC GTT TTA TAT ATG TTA AGA        1488

1489  GTT GTG TGA ACT TAA ATT TTA AGA GAT TGC TTA CAA GTC AAG TTA AAC        1536

1537  AAA ATA TAT CTT TTT TCT AGA AGA TTT AGT ATT TAT GAG TAT AAT ATA        1584

1585  TTT AGC ATT TAT TAG CAT AAT ATA TTT GAA TTT GAT TAG AAT TAG GTT        1632

1633  TTT TCA ACC TAT AAA TAG ATG TAG TCA AAA CTC CTC TTG TAA TCA TTC        1680

1681  GAA TTT GAC ATA GTG AAT TC                                             1700
```

FIG.2C

| | | |
|---:|:---|---:|
| 1 | GG TAC CAA ACA ATT AAG TAT TGA TAC CAG ACC CTT AAA TTT GAA ATT | 47 |
| 48 | TTA CAA TTC AGT CTT ATT TCA TGC TCA AAC TTC ACA ATT AGG CCA TTG | 95 |
| 96 | TTT GTT TAA TTT AAT GGA ATT GGA ATG TAC GTG TAT TTA TAA TTG TAT | 143 |
| 144 | GGT TTA AAT AGA AGT ATG AAA TAT TTG ATG AGA GTT GTC TCG GCA ATA | 191 |
| 192 | AAT TTG ACA TTC TGT TAT TTG GAC TCA GCG ATT GAG TCG GAT AAT TTA | 239 |
| 240 | GGT GTT ACA ATA TGT ATT TCA TAT TTG GCA AAA ATA AAG TGA GAG TAA | 287 |
| 288 | TGA AAG ATT GAA TTA AGG GAA ACT ATA TTT GAT AGC CAT CTT TGA TTG | 335 |
| 336 | GTA AAG CTA CTA ATA TCA GAA AAC CGG AAA AAC TAC TAT TAT AAA AAA | 383 |
| 384 | GAA AAC CGG AAC ACT AAG CAT GCT AAT ATT ATG CAT TAA TCA AGG GAG | 431 |
| 432 | TAA TTC AGC ATT AGT GAT GAA GAT GAA AGT GGT CGA TAC AAA CCT TTT | 479 |
| 480 | CCA AAG CAT TAA ACA CAC TCA ACC ATA AGC TGA AAC ATG AAA AAG AAA | 527 |
| 528 | GAA AGA AAC CTT GGC ATT AAA TTG GGC CAG CTA CCA GCG CCT AAC CAT | 575 |
| 576 | ATT CTA TTC GTA CGT GTT TCT CGG TTC TTT CCA AAT CCC TTC ACT CGA | 623 |
| 624 | CTT TTG GCT ATA ATA ACC CTC CTA CCT TCA ATC CTT ATC CAC GCA ACA | 671 |

FIG.3A

| | | | | | | | | | | | | | | | | |
|---|---|---|---|---|---|---|---|---|---|---|---|---|---|---|---|---|
| 672 | ATC | AGC | AAT | AGT | ACT | ACT | ACT | CCA | AGC | GAG | CAT | TTT | CCT | TAC | AAG | TTT | 719 |
| 720 | GTT | TTC | TTG | TGA | CTA | ATT | GAT | ATG | GCT | AGC | TCA | ATG | TCC | CTT | AAG | CTT | 767 |
| 1 | | | | | | | M | A | S | S | M | S | L | K | L | 9 |
| 768 | ACA | TGT | GTG | GTG | GTG | TTT | TGC | ATG | GTG | GTG | GGT | GCA | CCC | CTG | GCT | CAA | 815 |
| 10 | T | C | V | V | V | F | C | M | V | V | G | A | P | L | A | Q | 25 |
| 816 | GGG | GCC | ATA | AGT | TGT | GGT | CAA | ATC | ACA | AGC | GCC | CTC | GCA | CCC | TGC | ATT | 863 |
| 26 | G | A | I | S | C | G | Q | I | T | S | A | L | A | P | C | I | 41 |
| 864 | GCT | TAC | TTG | AAA | GGG | AAT | GGT | GCT | GGT | TCT | GCT | CCC | CCA | GCT | TGC | TGC | 911 |
| 42 | A | Y | L | K | G | N | G | A | G | S | A | P | P | A | C | C | 57 |
| 912 | AAC | GGC | ATC | AGA | TCT | CTC | AAC | TCT | GCC | GCC | AAA | ACA | ACA | CCA | GAC | CGG | 959 |
| 58 | N | G | I | R | S | L | N | S | A | A | K | T | T | P | D | R | 73 |
| 960 | CAA | CGA | GCT | TGC | AGC | TGC | ATC | AAA | AGT | GCG | GCC | ACC | GGC | ATT | TCT | GGC | 1007 |
| 74 | Q | R | A | C | S | C | I | K | S | A | A | T | G | I | S | G | 89 |
| 1008 | ATC | AAC | TAT | AGC | ACT | GCA | GCC | GGA | CTC | CCA | GGC | AAG | TGC | GGT | ATC | AAC | 1055 |
| 90 | I | N | Y | S | T | A | A | G | L | P | G | K | C | G | I | N | 105 |
| 1056 | ATC | CCT | TAC | AAG | ATC | AGC | CCT | TCC | ACT | GAC | TGC | AAA | AGG | TTC | GTA | TCT | 1103 |
| 106 | I | P | Y | K | I | S | P | S | T | D | C | K | R | | | | 118 |
| 1104 | AAT | TTA | AAC | TAG | GTT | TCT | TTG | AAA | TTA | CGG | AAA | AAG | AAA | ATG | ACC | CAA | 1151 |

(intron marker between positions 1091–1094 region)

FIG.3B

```
1152  AGT TTA TCG CTT ATG GCA ATT GAT TTA TTA ATT TAT GAA TGT TTT GTT         1199

1200  TGG TGT GGT TGC ATT TGC AGC ATT AAG TGA AGT GTG GTC ATG GAA GTT         1247
                          I   K   *                                          121

1248  GGG ATC AGC TAA TGG AAG GGA AAT AGT GAT GTC GAC AGA ATA AAA ATG         1295

1296  AAT GTT AAA AAT CCA TAG CGG TAC TAT TCA TTG TTG GAG TTA TCC TAG         1343

1344  TTT TAG AGT TAG TGG TAA TGT ACA AGG TCG CAT ATG CGA CTA TAT AAT         1391

1392  ACT ATC TTT ACC TAC TCT AAA TAT TAA TAT CAC TCT CAC TAG TTG TTT         1439

1440  CCT CTA TAT ATA CTC TTC ATT TCC TTT TCT TTT TCT TTT TTT TTT TTT         1487

1488  TTG TCC TGC GTG ACG ATT TCA AGC ATT TCA TAT AAA CAC CCA CGT GAT         1535

1536  CTA ACG ATA ATT AAA ACC ACG TTA ATC ACT AAA AAA ACT AAG AAT AAA         1583

1584  AGA AAT GGT GTT TAT ATT AGT ATT TAG AAT CTT GAT GAG TTG CTA TAC         1631

1632  CGG CGC ACA GTA GGA GGT GGT ACA CCA GCA GTA ATA AAA ATA ACC CAG         1679

1680  GAA ACA AGA AGT AGC AGT ATT ATG GGA TAA ATT TAA CAA AAA TGC TGA         1727

1728  AAA AAA GAG TTA TTT GAG TTA GTA TAA TTT TTT TTT AAA TTT ATT GAT         1775
```

FIG.3C

```
1776  TTA CAT TGT TTA CGA AGA AAG AAT AAC GTG TCG TAC GAG GTG TAT TTT    1823

1824  CAT TGA TGT GGC AAT GAA AAT GCG CCG GTA GGA CCC ATT TTT ACT TTG    1871

1872  CTA AAA TTT ATT TTT TTC TTT TTT TTT CTT GCA ATT TGA AAT TAG AAG    1919

1920  TTT GAA CAT TTA TTT TCA TTC TTG TTT GAG ATA GAC ACT GTT ATA GTT    1967

1968  TTA AGG AAT GTT TGA ATT TAT GGT GGT GTC GTG GAG TTA GGT GAC CCT    2015

2016  CAA ATT TCA TTG TCA TGT GAG TAT GGC GCC ATC ACC CGA GAA GCC AGA    2063

2064  TCG CAT TGC AAC TCA TGG TCC CAG TAA GGG TGA TTA TAC GGT CTG AAA    2111

2112  TTG AAG TGT AAC TAG AGC TTC AAG TTT ACA AAA TGT TAC GCT ATC AAA    2159

2160  GGA CGG AGT ATG ATT GGA GCT GTA ATT TAC AAT GGT TAT ACG GGC ACG    2207

2208  ACA AAA AAC TTT TTT CAT TAG AAA ATG ATG CTT TAT AAA ACT CAT ACA    2255

2256  CAA GTA CGA GGA AGA AAA AAT GGC AAT GGT ATC TCA GTA TAA TTA AGT    2303

2304  AAA TTT TTT TAT CCA TCT CCA CCA AAG ACA GTG ACA CCG TTA CTA TTA    2351

2352  CCT ATG ATA GAA TTG GGA TGT AAT AGG TTT TAG TAA CAG GGT CAT TGC    2399

2400  CTT TGC TGG AAA AGG ATA AAA TGA ATT ACT TGA TTA TAC TGG AAG ACC    2447
```

FIG.3D

```
2448  CCT GTG ATT TTC TCC CTC GTA CTT GTA TAT GGA TTT TAT AAA GTA TGC         2495

2496  TCT TCC AAT GAG GAA AAA CTA GTT CTT GTG CTT GCA TCA CCG TCG TCA         2543

2544  ACT ACA GTC CCG GTT TTG CTC CAT CCT TTT AAT AGC ATA ACC TTT GTA         2591

2592  AAC TTG AAG CCT TAT TTA CAC CGT CAA CTT GGA CCT CGA GGG GGG GCC         2639

2640  CGG TAC C                                                                2646
```

FIG.3E

FIBER-SPECIFIC PROTEIN EXPRESSION IN THE COTTON PLANT

BACKGROUND OF THE INVENTION

1. Field of the Invention

The present invention is related to plant genetic engineering. In particular, the present invention is related to a DNA sequence which can promote gene expression in cotton plants (*Gossypium hirsutum* L.) in a tissue-specific manner.

2. Discussion of the Background

Cotton fiber development is divided into four stages: initiation, elongation, secondary cell wall synthesis, and maturation. The elongation phase, during which primary cell wall synthesis occurs, is marked by rapid, unidirectional expansion of the primary cell wall. In order to support rapid primary cell wall expansion during the 15 to 20 day course of fiber elongation, cellular machinery must synthesize large amounts of lipids, such as cutin.

Lipid transfer proteins have been implicated in the process of cotton fiber primary cell wall synthesis. Like other classes of exported proteins, lipid transfer proteins contain a highly hydrophobic signal peptide. Lipid transfer proteins are secreted from the fiber cell and reside either in the cell wall or in the outer cellular layer of the fiber cell. Lipid transfer proteins appear to participate in the intracellular transport of lipids for in vivo membrane biosynthesis.

Although the nucleus of every cell contains the entire complement of genomic DNA, a cell in a given tissue does not express every single gene in the genome. Rather, a given cell expresses a population of genes which code for proteins that are critical for maintaining cellular physiology. The challenge every cell faces is to express thousands of different genes at exactly the right times and in exactly the right amounts to prevent cellular physiology from becoming compromised.

Tissue-specific gene expression is often regulated at the level of gene transcription. Transcription is the process by which double-stranded DNA is read into single-stranded RNA. The processes of transcription initiation, and regulation of subsequent changes in rates of transcription reinitiation, are controlled by protein-DNA interactions.

Transcription is a highly regulated process in which nuclear gene regulatory proteins (often called transcription factors) bind, with high affinity, to short (five to fifteen base pair) lengths of DNA sequence known as regulatory elements. Protein-DNA interactions occur in the promoter, 5' flanking, and 3' flanking regions of the gene. Through such protein-DNA interactions, gene expression is programmed to respond to changes in extracellular signals such as light, temperature, growth factor concentration, hormone concentration, and drug concentration. Transcription is also regulated by changes in intracellular signals such as second messenger concentration and post-translational modification of protein (level of phosphorylation, myristylation, etc.). Such transcriptional mechanisms regulate tissue-specific protein expression.

Gene expression techniques are well known for mammalian systems. In comparison, very few are known for plant systems. For example, the ability to genetically transform cotton fibers has only recently been determined. Umbeck et al. (U.S. Pat. Nos. 5,004,863 and 5,159,135) describe Agrobacterium-mediated genetic transformation of cotton tissues.

A cotton gene promoter, E6, has recently been discovered which confers tissue and temporal specificity to gene expression in transgenic cotton plants, demonstrating that some plant promoters can be used to drive gene expression in plants in a tissue-specific manner (John & Petersen, *Plant Molecular Biology*, 1994, 26:1989; John & Crow, *Proc. Natl. Acad. Sci. USA*, 1992, 89:5769).

Accordingly, there is a continuing need to uncover other expression systems for plant systems, in particular for cotton plants.

SUMMARY OF THE INVENTION

Accordingly, one object of the present invention is to provide a DNA sequence which can be used to promote gene expression in cotton plants (*Gossypium hirsutum* L.).

A second object of the present invention is to provide the nucleotide and amino acid sequences for the GH3 lipid transfer protein.

A third object of the present invention is to provide the 5' flanking sequence of GH3 as well as that of the lipid transfer proteins PLTP6 and PLTP12.

It is still further an object of the present invention to provide a method for directing the expression of a biologically useful product in *Gossypium hirsutum* L.

The present inventors have now found that gene expression in cotton fibers can be directed by positioning the nucleotide sequences 5' of the genes encoding the lipid transfer proteins GH3, PLTP6 and PLTP12 upstream of a gene encoding a biologically useful product.

BRIEF DESCRIPTION OF THE FIGURES

A more complete appreciation of the invention and many of the attendant advantages thereof will be readily obtained as the same become better understood by reference to the following detailed description when considered in connection with the accompanying drawings, wherein:

FIG. 1 shows the nucleotide (identified by bases 7–615 of SEQ ID NO: 1) and amino acid sequence (SEQ ID NO:2) of the GH3 lipid transfer protein.

FIG. 2 (A, B, and C) shows the nucleotide (SEQ ID NO:3) and amino acid sequence (SEQ ID NO:4) of the PLTP6 lipid transfer protein as well as promoter and upstream sequences.

FIG. 3 (A, B, C, D, and E) shows the nucleotide (SEQ ID NO:5) and amino acid sequence (SEQ ID NO:6) of the PLTP12 lipid transfer protein as well as promoter and upstream sequences.

DETAILED DESCRIPTION OF THE PREFERRED EMBODIMENTS

The nucleotide sequence encoding the GH3 lipid transfer protein is nucleotide 78 to 437 in FIG. 1. The GH3 protein contains a hydrophobic signal sequence (amino acid residues 1 to 26 in FIG. 1) as well as an extracellular domain (amino acid residues 27 to 120 in FIG. 1). This protein facilitates primary cell wall development by transporting phospholipids across the cell membrane to the exterior of the cell.

The gene encoding GH3, when cloned into a suitable expression vector, can be used to express the lipid transfer protein in a plant expression system. Recombinant GH3 protein can be used to generate monoclonal or polyclonal antibodies useful in Western analysis, in radioimmunoassay, in other assays of protein-protein interaction, or to screen tissue samples for evidence of GH3 protein expression or other lipid transfer protein expression. The DNA sequence encoding the GH3 protein can also be used as a probe to screen plant cDNA expression libraries for homologous lipid transfer proteins.

The region referred to herein as the "5' flanking sequence of GH3" comprises at least 0.5 kb 5' to nucleotide 78 in FIG. 1. The 5' flanking sequence preferably comprises positions 1 to 78 in FIG. 1. This sequence is useful for directing the tissue-specific and temporal-specific expression of lipid transfer proteins.

It is expected that 5' and 3' DNA sequences flanking genes encoding homologous lipid transfer proteins will also be useful for directing expression of lipid transfer proteins.

The promoter and upstream sequences of either the PLTP6 or the PLTP12 gene can also be used in accordance with the present invention.

The 5' flanking regions of PLTP6 (positions 1–448) and PLTP12 (positions 1–741) contain regulatory elements which can direct the expression of lipid transfer protein in cotton fiber cells.

The nucleotide sequences of the present invention can be used to direct expression of any known gene of interest. Biologically useful products that can be expressed in cotton fibers include, but are not limited to: amino acids (such as isoleucine, lysine, tyrosine, etc), the GH3 lipid transfer protein (see FIG. 1), Bacillus thuringiensis toxins (Klier et al. in Molecular Biology of Microbial Differentiation. Eds: Hoch, J. A. and Setlow, P., pp. 217–224, 1985), viral coat proteins, ketothiolase, acetoacetyl-CoA reductase, or poly-betahydroxybutyric acid synthase (Peoples and Sinskey, J. Biol. Chem. 1989, 264: 15293–15297). Negative strand RNA transcription (Mol et al., FEBS Lett., 1990, 268:427–430; Van der Krol et al., Gene. 1988, 72:45–50) in cotton plant cells can be used to inhibit undesirable endogenous genes and facilitate selection of disease resistance traits.

Expression of these biologically useful products can confer particular advantages over other known cotton plants. Such advantages include resistance to drought, resistance to frigid temperature, resistance to high temperatures, resistance to infection by harmful plant parasites, and resistance to soil nutrient depletion. Further advantages include enhanced interaction with helpful plant parasites, a shorter growing season (permitting more frequent cotton harvests), and alterations in cotton fiber physical properties.

The method of the present invention comprises:
  (a) introducing into a cotton plant cell a vector comprising
    (i) a GH3 5' flanking region, a PLTP6 promoter and upstream sequence, or a PLTP12 promoter and upstream sequence operably linked to (ii) a biologically useful protein-encoding gene; and
  (b) germinating the cotton plant cell into a cotton plant.

Suitable vectors containing the nucleotide sequences of the present invention operably linked to a biologically useful protein-encoding gene can be constructed using techniques well known in the art (See, for example, Basic Methods in Molecular Biology, Eds: Davis, D. et al. Appleton and Lange, pp. 278–290, 1994). "Operably linked" means that the nucleotide sequence is linked so as to promote expression of the biologically useful product. Typically, the nucleotide sequence will be directly 5' adjacent to the gene encoding the biologically useful product in the proper reading frame.

Vectors in accordance with the present invention can further comprise selectable markers such as antibiotic resistance genes (such as the neomycin phosphotransferase II gene which codes for resistance to kanamycin, the aminoglycoside phosphotransferase e'-IV gene which codes for resistance to Hygromycin B, Chloramphenicol acetyl transferase gene which codes for resistance to chloramphenicol, etc.) so that the appropriate antibiotic can be used to segregate and select transformed cells. Preferred vectors include pBI121 and pBI221.

Suitably, vectors in accordance with the present invention can be introduced into cotton fiber cells as described by Umbeck et al., U.S. Pat. Nos. 5,004,863 and 5,159,135; incorporated herein by reference. Selection of transformed cotton fiber cells is also described therein.

Germination of the transformed cotton fiber cell into a cotton fiber plant can be performed in accordance with techniques well known in the art (See for example Umbeck, U.S. Pat. Nos. 5,004,863 and 5,159,135; incorporated herein by reference).

Having generally described this invention, a further understanding can be obtained by reference to certain specific examples which are provided herein for purposes of illustration only and are not intended to be limiting unless otherwise specified.

EXAMPLES

Isolation of cDNA encoding the lipid transfer protein GH3

A cotton (Gossypium hirsutum L. cultivar DES119) fiber cDNA library was constructed in lambda gt10 using a PCR-based method (Belyavsky et al., Nucl. Acids Res., 1989, 17:2919) and twenty-six fiber-specific cDNA clones were subsequently isolated using a differential screening method (Sargent, Methods Enzymol., 1987, 152:423). One full-length clone, GH3, and several GH3-related cDNA clones were obtained, subcloned into M13 (Messing, Gene, 1982, 19:269) and sequenced using the dideoxy chain termination method (Sanger et al., Proc. Natl. Acad. Sci. USA, 1977, 74:5463). The nucleotide sequence and predicted amino acid sequence for the GH3 protein is shown in FIG. 1 (SEQ ID NOS: 1 & 2).

Characterization of the lipid transfer protein GH3

GH3 encodes a polypeptide of 120 amino acids with a calculated molecular weight of 11,844 Dalton. This polypeptide is a putative lipid transfer protein. GH3 contains an amino acid sequence which is homologous to lipid transfer protein sequences in spinach (Bouilion et al. Eur. J. Biochem., 1987, 166:387), maize (Tchang et al, J. Biol. Chem., 1988, 263:16849), tobacco (Masuta et al, FEBS Lett., 1992, 311:119), tomato (Torres-Schumann et al, Plant Mol. Biol., 1992, 18:749), carrot (Sterk et al, Plant Cell, 1991, 3:907) and rice (Yu et al, Arch. Biochem. Biophys., 1988, 265:466) and shares amino acid identities of 60%, 56%, 55%, 55%, 54% and 51%, respectively, with these proteins.

Plant lipid transfer proteins, in general, are characterized by low molecular mass (9–11 kDa), High (basic) isoelectric point, low levels of aromatic amino acids (Phe, Trp, and Tyr), a high level of proline, and seven to eight conserved cysteine residues which are involved in the formation of disulfide bonds. The GH3 fiber lipid transfer protein has all of these structural features. In addition, the GH3 protein also contains an RQ motif (residues 73 and 74), which has been suggested to be the binding site for phospholipid phosphate groups.

The hydrophobic domain, LPGKCGVNIPY (SEQ ID NO:7) (residues 98 to 108) is the possible binding site of the two acyl chains (Tchang et al. J. Biol. Chem., 1988, 263:16849). Similar to other plant cDNA and gene sequences for lipid transfer proteins, the GH3 protein also contains a highly hydrophobic signal peptide of 26 amino acids, which is characteristic of exported proteins.

To characterize GH3 expression during fiber development, a Northern analysis was performed. Equal amounts of total RNA, isolated from leaves, roots, flowers, and fibers at different developmental stages, were electrophoresed, blotted, and hybridized with a $^{32}$p-labeled, M13 single-stranded GH3 DNA probe. The probe hybridized strongly to an RNA specie of approximately 0.9 kb. During fiber elongation, GH3 expression increased and reached a maximum at fifteen days postanthesis (DPA). The message level decreased sharply after 20 DPA, the stage of secondary cell wall synthesis. The GH3 mRNA was also detected, albeit at a low level, in the leaf. Even after long exposures, however, the GH3 signal was not detectable in the root or in the flower. These results clearly indicate that the Ltp gene is differentially expressed in cotton fiber cells, in both temporal and spatial fashions.

Since the 0.9 kb fiber RNA band appeared to be very broad, the presence of two similar sizes of LTP mRNAs could not be excluded. Results of Southern analysis suggested that the cotton Ltp gene is present in a few copies. Single copies of Ltp gene have been reported in spinach (Bernhard et al., Plant Physiol., 1991, 95:164), tomato (Torres-Schumann et al., Plant Mol. Biol., 1992, 18:749), and carrot (Sterk et al., Plant cell, 1991, 3:907). In contrast, several Ltp genes were found in barley (Gausing, Planta 192:574, 1994) and castor bean (Tsuboi et al, J. Biochem. 110:823, 1991).

The 5' flanking sequence of GH3 gene containing regulatory elements will be dissected by an E. coli GUS (β-glucuronidase) reporter gene system. The 5' flanking region will be fused to the GUS gene in a binary vector and transferred to cotton via Agrobacterium-mediated transformation or particle bombardment. Promoter function and DNA sequences for fiber specific expression will be identified by determining GUS activity in fiber cells.

Having now fully described the invention, it will be apparent to one of ordinary skill in the art that many changes and modifications can be made thereto without departing from the spirit or scope of the invention as set forth herein.

What is claimed is:

1. An isolated DNA molecule having the nucleotide sequence of SEQ ID NO:1, 3, or 5.

2. A vector comprising a DNA molecule having the nucleotide sequence of SEQ ID NO:1, 3, or 5 operably linked to a gene encoding a biologically useful product.

3. The vector of claim 2, further comprising a selectable marker.

4. A cotton seed capable of germination into a cotton plant containing a vector comprising a DNA molecule having the nucleotide sequence of SEQ ID NO:1, 3, or 5 operably linked to a gene encoding a biologically useful product.

5. Cotton plants germinated from the seeds of claim 4.

6. A method of expressing a biological product in a cotton plant cell which comprises:

(a) introducing into said cotton plant cell a vector comprising a nucleotide sequence of SEQ ID NO:1, 3, or 5 operably linked to a gene encoding a biologically useful protein; and (b) germinating the cotton plant cell into a cotton plant.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 615 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 84..443

( x i ) SEQUENCE DESCRIPTION: SEQ ID NO:1:

```
CCATTGGACG ACAATCACCA ATAGTTCTAC TACTCCAAGC AAGTATTTTC CTTAGACGTT        60

TGTTTTCTT GTGATTAATC GAT ATG GCT AGC TCA ATG TCC CTT AAA CTT           110
              Met Ala Ser Ser Met Ser Leu Lys Leu
                1               5

GCA TGT GTG GTG GTG TTG TGC ATG GTA GTG GGT GCA CCC CTG GCT CAA        158
Ala Cys Val Val Val Leu Cys Met Val Val Gly Ala Pro Leu Ala Gln
 10              15              20              25

GGG GCC GTA ACC TCT GGT CAA GTC ACA AAC TCC CTC GCA CCC TGC ATT        206
Gly Ala Val Thr Ser Gly Gln Val Thr Asn Ser Leu Ala Pro Cys Ile
             30              35              40

AAT TAC TTG AGA GGC AGT GGT GCT GGT GCC GTT CCC CCA GGT TGC TGC        254
Asn Tyr Leu Arg Gly Ser Gly Ala Gly Ala Val Pro Pro Gly Cys Cys
         45              50              55

ACG GGC ATC AAA TCT CTC AAC TCC GCC GCC CAA ACA ACA CCA GTC CGG        302
Thr Gly Ile Lys Ser Leu Asn Ser Ala Ala Gln Thr Thr Pro Val Arg
     60              65              70

CAA GCA GCT TGC AGA TGC ATC AAA AGT GCG GCC GCC GGC ATT ACT GGC        350
Gln Ala Ala Cys Arg Cys Ile Lys Ser Ala Ala Ala Gly Ile Thr Gly
 75              80              85

ATC AAC TTT GGC CTT GCA AGC GGA CTC CCA GGC AAG TGC GGT GTC AAC        398
Ile Asn Phe Gly Leu Ala Ser Gly Leu Pro Gly Lys Cys Gly Val Asn
 90              95              100             105

ATC CCT TAC AAG ATC AGC CCT AGC ACT GAC TGC AAC AGC GTC AAG            443
```

| Ile | Pro | Tyr | Lys | Ile | Ser | Pro | Ser | Thr | Asp | Cys | Asn | Ser | Val | Lys |
|---|---|---|---|---|---|---|---|---|---|---|---|---|---|---|
| | | | | 110 | | | | | 115 | | | | | 120 |

| | | | | | |
|---|---|---|---|---|---|
| TGAAGTTTTG | GCATGGAAAG | TTCACCAGCT | AGTGGAAGCC | AAAATAACGA | TAGCTACAGA | 503 |
| ATAAATATGG | ATGTTAAAAT | TCCAGAGTTA | TGCGTTGTGT | ACTATGCCGC | TTTATGCGAC | 563 |
| TACGTAATAT | AATCTTTATC | TACAAATTAG | TATCAAAAAA | AAAAAAAAAA | AA | 615 |

( 2 ) INFORMATION FOR SEQ ID NO:2:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Ser | Ser | Met | Ser | Leu | Lys | Leu | Ala | Cys | Val | Val | Val | Leu | Cys |
|---|---|---|---|---|---|---|---|---|---|---|---|---|---|---|---|
| 1 | | | | 5 | | | | | 10 | | | | | 15 | |

| Met | Val | Val | Gly | Ala | Pro | Leu | Ala | Gln | Gly | Ala | Val | Thr | Ser | Gly | Gln |
|---|---|---|---|---|---|---|---|---|---|---|---|---|---|---|---|
| | | | 20 | | | | | 25 | | | | | 30 | | |

| Val | Thr | Asn | Ser | Leu | Ala | Pro | Cys | Ile | Asn | Tyr | Leu | Arg | Gly | Ser | Gly |
|---|---|---|---|---|---|---|---|---|---|---|---|---|---|---|---|
| | | 35 | | | | | 40 | | | | | 45 | | | |

| Ala | Gly | Ala | Val | Pro | Pro | Gly | Cys | Cys | Thr | Gly | Ile | Lys | Ser | Leu | Asn |
|---|---|---|---|---|---|---|---|---|---|---|---|---|---|---|---|
| | 50 | | | | | 55 | | | | | 60 | | | | |

| Ser | Ala | Ala | Gln | Thr | Thr | Pro | Val | Arg | Gln | Ala | Ala | Cys | Arg | Cys | Ile |
|---|---|---|---|---|---|---|---|---|---|---|---|---|---|---|---|
| 65 | | | | | 70 | | | | | 75 | | | | | 80 |

| Lys | Ser | Ala | Ala | Ala | Gly | Ile | Thr | Gly | Ile | Asn | Phe | Gly | Leu | Ala | Ser |
|---|---|---|---|---|---|---|---|---|---|---|---|---|---|---|---|
| | | | | 85 | | | | | 90 | | | | | 95 | |

| Gly | Leu | Pro | Gly | Lys | Cys | Gly | Val | Asn | Ile | Pro | Tyr | Lys | Ile | Ser | Pro |
|---|---|---|---|---|---|---|---|---|---|---|---|---|---|---|---|
| | | | 100 | | | | | 105 | | | | | 110 | | |

| Ser | Thr | Asp | Cys | Asn | Ser | Val | Lys |
|---|---|---|---|---|---|---|---|
| | | 115 | | | | | 120 |

( 2 ) INFORMATION FOR SEQ ID NO:3:

( i ) SEQUENCE CHARACTERISTICS:
        ( A ) LENGTH: 1700 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: intron
        ( B ) LOCATION: 801..936

( i x ) FEATURE:
        ( A ) NAME/KEY: CDS
        ( B ) LOCATION: join(448..800, 937..943)

( x i ) SEQUENCE DESCRIPTION: SEQ ID NO:3:

| | | | | | | |
|---|---|---|---|---|---|---|
| GAATTCCCCT | TCTGTTTTAG | TTGTCTTTCT | TCATCTTTTC | CCTTTTCTGC | AAGCATGCAA | 60 |
| TTGTGTTGTA | CGGTAAGTTT | CTGTTTTATT | AAACTTAAAT | GTTACTCTGG | ATAAGGGATT | 120 |
| AAGGGGTGTT | TTGTTGACTG | TTTAGGAGTC | GATCGTGAGG | CTGGAATTAA | CGTTCATCTA | 180 |
| TTTGACTCGA | AGTGGTGATC | GTTGGTAAG | TGTACAAGGT | ATGCGTTTCT | ATGTGTTGGG | 240 |
| CGAGTGGTTT | GGCATTGAAT | TAGGGCAACT | AACAGGCACC | AATGCCTAAC | CAAGTTGTAT | 300 |
| TCGTACGCCT | TTCTTAGTTT | TTTTTCCAT | ATTCCTTCAC | TCAACTTTTG | TCTATAAAAA | 360 |
| CCCTCCAACC | AGCAATCCCA | TTACTAATAC | TCCACCACT | TTCTTACAAG | TTGGTAAAAT | 420 |

| | | | | | | | | | | | | | | | | |
|---|---|---|---|---|---|---|---|---|---|---|---|---|---|---|---|---|
| TATTAGTTTT | TCTTGTAATT | AATCGAT | ATG<br>Met<br>1 | GCT<br>Ala | AGG<br>Arg | TCA<br>Ser | ATG<br>Met<br>5 | TCT<br>Ser | CTT<br>Leu | AAG<br>Lys | | | | | | 471 |
| CTT<br>Leu | GCA<br>Ala<br>10 | TGT<br>Cys | GTA<br>Val | GTG<br>Val | GTG<br>Val | TTG<br>Leu<br>15 | TGC<br>Cys | TTG<br>Leu | TTG<br>Leu | GTG<br>Val | GAT<br>Asp<br>20 | GCA<br>Ala | CCC<br>Pro | CTG<br>Leu | GCT<br>Ala | 519 |
| CAA<br>Gln<br>25 | GGG<br>Gly | GCC<br>Ala | ATA<br>Ile | AGC<br>Ser | TAT<br>Tyr<br>30 | GAT<br>Asp | CAA<br>Gln | GTC<br>Val | AAA<br>Lys | TCC<br>Ser<br>35 | TCC<br>Ser | CTC<br>Leu | CTA<br>Leu | CCC<br>Pro | TGC<br>Cys<br>40 | 567 |
| GTT<br>Val | GGT<br>Gly | TAC<br>Tyr | GTG<br>Val | AGA<br>Arg<br>45 | GGT<br>Gly | AAT<br>Asn | AAT<br>Asn | GCT<br>Ala | CGT<br>Arg<br>50 | CCT<br>Pro | GCT<br>Ala | CCC<br>Pro | CCA<br>Pro | AAT<br>Asn<br>55 | TAC<br>Tyr | 615 |
| TGT<br>Cys | AAA<br>Lys | GGC<br>Gly | ATC<br>Ile<br>60 | AGA<br>Arg | TCT<br>Ser | CTC<br>Leu | AAA<br>Lys | TCT<br>Ser<br>65 | GCC<br>Ala | GCC<br>Ala | CGA<br>Arg | ATA<br>Ile | AGA<br>Arg<br>70 | CTA<br>Leu | GAT<br>Asp | 663 |
| CGG<br>Arg | CAA<br>Gln | GCA<br>Ala<br>75 | GCT<br>Ala | TGT<br>Cys | AAA<br>Lys | TGC<br>Cys | ATC<br>Ile<br>80 | AAA<br>Lys | AGT<br>Ser | CTG<br>Leu | GCC<br>Ala | GCC<br>Ala<br>85 | GAC<br>Asp | ATT<br>Ile | TCT<br>Ser | 711 |
| GAC<br>Asp | ATC<br>Ile<br>90 | AAC<br>Asn | TAT<br>Tyr | GGC<br>Gly | GTT<br>Val | GCA<br>Ala<br>95 | GCC<br>Ala | GGA<br>Gly | CTC<br>Leu | CCA<br>Pro | GGC<br>Gly<br>100 | CAG<br>Gln | TGC<br>Cys | AAC<br>Asn | GTC<br>Val | 759 |
| CAC<br>His<br>105 | ATC<br>Ile | CCT<br>Pro | TAC<br>Tyr | AAG<br>Lys | ATC<br>Ile<br>110 | AGC<br>Ser | CCT<br>Pro | AGC<br>Ser | ATT<br>Ile | GAC<br>Asp<br>115 | TGC<br>Cys | AAA<br>Lys | AG<br>Arg | | | 800 |
| GTTCGTATCT | AATTTAAGCT | AGACTTCATT | GAAATTACGA | AAAAGAAAAT | GGCCCCAAAT | | | | | | | | | | | 860 |
| TTGTTGCATA | ACATTAAGTG | AGTTTATTGA | TTAATTAATT | GATGAATGTT | TTACTTTGGT | | | | | | | | | | | 920 |
| GTGGTTGCAT | TTGCAG A | GTC AAG<br>Val Lys<br>120 | TGACGTGTGG | CCATGGAAGT | TGGGATCAGC | | | | | | | | | | | 973 |
| TAATGGAAGG | GAAATGGTGG | TGTACTCACT | AAAAATTATC | CTAGTTTTAG | AGTTGGTGAC | | | | | | | | | | | 1033 |
| GATGTACAAG | GTCGATTTAT | GCGACTATCT | AATAATATCT | TTACCTACTC | AAAATATTAA | | | | | | | | | | | 1093 |
| TATCACTCTC | AATGGTTGTT | TCTTCTATGT | ATACACTCTT | CATTTCCCTT | TGCTTTGTTT | | | | | | | | | | | 1153 |
| TTTTTTCCAA | GTCAAGCGTA | CCATTTCAAG | CATTTCATAT | AAACACCCGC | GTGTCCTAAT | | | | | | | | | | | 1213 |
| GATAATGGAA | ACCCACGTGA | GCCAGATATG | GATGCTCAAT | TATTCGAAGA | TGAATGTATG | | | | | | | | | | | 1273 |
| GACCAGCATT | TTTAAGCAAT | AAGAATAAAT | AAATAAAAAT | TTCAAGTGAA | TTGAATACAA | | | | | | | | | | | 1333 |
| ATCTTAAATC | CTACGATGAA | TGAATACATC | ATTTAAATTT | AAAACAAAAA | AATTATTTAA | | | | | | | | | | | 1393 |
| ATAATTTCTT | TTTTTAATTT | TTTTAGTTGC | TCAAATGTGA | ATTATGAATA | GGTCTAAGAG | | | | | | | | | | | 1453 |
| TATTGTTGAG | CCAAGTCGTT | TTATATATGT | TAAGAGTTGT | GTGAACTTAA | ATTTTAAGAG | | | | | | | | | | | 1513 |
| ATTGCTTACA | AGTCAAGTTA | AACAAAATAT | ATCTTTTTTC | TAGAAGATTT | AGTATTTATG | | | | | | | | | | | 1573 |
| AGTATAATAT | ATTTAGCATT | TATTAGCATA | ATATATTTGA | ATTTGATTAG | AATTAGGTTT | | | | | | | | | | | 1633 |
| TTTCAACCTA | TAAATAGATG | TAGTCAAAAC | TCCTCTTGTA | ATCATTCGAA | TTTGACATAG | | | | | | | | | | | 1693 |
| TGAATTC | | | | | | | | | | | | | | | | 1700 |

( 2 ) INFORMATION FOR SEQ ID NO:4:

( i ) SEQUENCE CHARACTERISTICS:
        ( A ) LENGTH: 120 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met | Ala | Arg | Ser | Met | Ser | Leu | Lys | Leu | Ala | Cys | Val | Val | Val | Leu | Cys |
| 1 | | | | 5 | | | | | 10 | | | | | 15 | |

| Leu | Leu | Val | Asp | Ala | Pro | Leu | Ala | Gln | Gly | Ala | Ile | Ser | Tyr | Asp | Gln |
|---|---|---|---|---|---|---|---|---|---|---|---|---|---|---|---|
| | | | 20 | | | | | 25 | | | | | 30 | | |

| Val | Lys | Ser | Ser | Leu | Leu | Pro | Cys | Val | Gly | Tyr | Val | Arg | Gly | Asn | Asn |
|---|---|---|---|---|---|---|---|---|---|---|---|---|---|---|---|
| | | 35 | | | | | 40 | | | | | 45 | | | |

| Ala | Arg | Pro | Ala | Pro | Pro | Asn | Tyr | Cys | Lys | Gly | Ile | Arg | Ser | Leu | Lys |
|---|---|---|---|---|---|---|---|---|---|---|---|---|---|---|---|
| | 50 | | | | | 55 | | | | | 60 | | | | |

| Ser | Ala | Ala | Arg | Ile | Arg | Leu | Asp | Arg | Gln | Ala | Ala | Cys | Lys | Cys | Ile |
|---|---|---|---|---|---|---|---|---|---|---|---|---|---|---|---|
| 65 | | | | | 70 | | | | | 75 | | | | | 80 |

| Lys | Ser | Leu | Ala | Ala | Asp | Ile | Ser | Asp | Ile | Asn | Tyr | Gly | Val | Ala | Ala |
|---|---|---|---|---|---|---|---|---|---|---|---|---|---|---|---|
| | | | | 85 | | | | | 90 | | | | | 95 | |

| Gly | Leu | Pro | Gly | Gln | Cys | Asn | Val | His | Ile | Pro | Tyr | Lys | Ile | Ser | Pro |
|---|---|---|---|---|---|---|---|---|---|---|---|---|---|---|---|
| | | | 100 | | | | | 105 | | | | | 110 | | |

| Ser | Ile | Asp | Cys | Lys | Arg | Val | Lys |
|---|---|---|---|---|---|---|---|
| | | 115 | | | | | 120 |

( 2 ) INFORMATION FOR SEQ ID NO:5:

( i ) SEQUENCE CHARACTERISTICS:
    ( A ) LENGTH: 2646 base pairs
    ( B ) TYPE: nucleic acid
    ( C ) STRANDEDNESS: double
    ( D ) TOPOLOGY: linear ( i i ) MOLECULE TYPE: DNA (genomic)

( i x ) FEATURE:
    ( A ) NAME/KEY: CDS
    ( B ) LOCATION: join(741..1093, 1220..1226)

( i x ) FEATURE:
    ( A ) NAME/KEY: intron
    ( B ) LOCATION: 1094..1219

( x i ) SEQUENCE DESCRIPTION: SEQ ID NO:5:

```
GGTACCAAAC AATTAAGTAT TGATACCAGA CCCTTAAATT TGAAATTTTA CAATTCAGTC      60
TTATTTCATG CTCAAACTTC ACAATTAGGC CATTGTTTGT TAATTTAAT GGAATTGGAA      120
TGTACGTGTA TTTATAATTG TATGGTTTAA ATAGAAGTAT GAAATATTTG ATGAGAGTTG    180
TCTCGGCAAT AAATTTGACA TTCTGTTATT TGGACTCAGC GATTGAGTCG GATAATTTAG    240
GTGTTACAAT ATGTATTTCA TATTTGGCAA AAATAAAGTG AGAGTAATGA AAGATTGAAT    300
TAAGGGAAAC TATATTTGAT AGCCATCTTT GATTGGTAAA GCTACTAATA TCAGAAAACC    360
GGAAAAACTA CTATTATAAA AAGAAAACC GGAACACTAA GCATGCTAAT ATTATGCATT     420
AATCAAGGGA GTAATTCAGC ATTAGTGATG AAGATGAAAG TGGTCGATAC AAACCTTTTC    480
CAAAGCATTA AACACACTCA ACCATAAGCT GAAACATGAA AAAGAAAGAA AGAAACCTTG    540
GCATTAAATT GGGCCAGCTA CCAGCGCCTA ACCATATTCT ATTCGTACGT GTTTCTCGGT    600
TCTTTCCAAA TCCCTTCACT CGACTTTGG CTATAATAAC CCTCCTACCT TCAATCCTTA     660
TCCACGCAAC AATCAGCAAT AGTACTACTA CTCCAAGCGA GCATTTTCCT TACAAGTTTG    720
TTTTCTTGTG ACTAATTGAT ATG GCT AGC TCA ATG TCC CTT AAG CTT ACA         770
                        Met Ala Ser Ser Met Ser Leu Lys Leu Thr
                         1               5                   10
TGT GTG GTG GTG TTT TGC ATG GTG GTG GGT GCA CCC CTG GCT CAA GGG      818
Cys Val Val Val Phe Cys Met Val Val Gly Ala Pro Leu Ala Gln Gly
              15                  20                  25
GCC ATA AGT TGT GGT CAA ATC ACA AGC GCC CTC GCA CCC TGC ATT GCT      866
Ala Ile Ser Cys Gly Gln Ile Thr Ser Ala Leu Ala Pro Cys Ile Ala
         30                  35                  40
```

| | | | | | | | | | | | | | | |
|---|---|---|---|---|---|---|---|---|---|---|---|---|---|---|
| TAC | TTG | AAA | GGG | AAT | GGT | GCT | GGT | TCT | GCT | CCC | CCA | GCT | TGC | TGC | AAC | 914 |
| Tyr | Leu | Lys | Gly | Asn | Gly | Ala | Gly | Ser | Ala | Pro | Pro | Ala | Cys | Cys | Asn |
| | | 45 | | | | | 50 | | | | | 55 | | | |

| GGC | ATC | AGA | TCT | CTC | AAC | TCT | GCC | GCC | AAA | ACA | ACA | CCA | GAC | CGG | CAA | 962 |
| Gly | Ile | Arg | Ser | Leu | Asn | Ser | Ala | Ala | Lys | Thr | Thr | Pro | Asp | Arg | Gln |
| | 60 | | | | | 65 | | | | | 70 | | | | |

| CGA | GCT | TGC | AGC | TGC | ATC | AAA | AGT | GCG | GCC | ACC | GGC | ATT | TCT | GGC | ATC | 1010 |
| Arg | Ala | Cys | Ser | Cys | Ile | Lys | Ser | Ala | Ala | Thr | Gly | Ile | Ser | Gly | Ile |
| 75 | | | | | 80 | | | | | 85 | | | | | 90 |

| AAC | TAT | AGC | ACT | GCA | GCC | GGA | CTC | CCA | GGC | AAG | TGC | GGT | ATC | AAC | ATC | 1058 |
| Asn | Tyr | Ser | Thr | Ala | Ala | Gly | Leu | Pro | Gly | Lys | Cys | Gly | Ile | Asn | Ile |
| | | | | 95 | | | | | 100 | | | | | 105 | |

| CCT | TAC | AAG | ATC | AGC | CCT | TCC | ACT | GAC | TGC | AAA | AG | | GTTCGTATCT | | | 1103 |
| Pro | Tyr | Lys | Ile | Ser | Pro | Ser | Thr | Asp | Cys | Lys | Ser |
| | | | 110 | | | | | 115 | | | |

```
AATTTAAACT  AGGTTTCTTT  GAAATTACGG  AAAAAGAAAA  TGACCCAAAG  TTTATCGCTT    1163
ATGGCAATTG  ATTTATTAAT  TTATGAATGT  TTGTTTGGT   GTGGTTGCAT  TTGCAG C      1220
ATT  AAG    TGAAGTGTGG  TCATGGAAGT  TGGGATCAGC  TAATGGAAGG  GAAATAGTGA    1276
Ile  Lys
     120
TGTCGACAGA  ATAAAAATGA  ATGTTAAAAA  TCCATAGCGG  TACTATTCAT  TGTTGGAGTT    1336
ATCCTAGTTT  TAGAGTTAGT  GGTAATGTAC  AAGGTCGCAT  ATGCGACTAT  ATAATACTAT    1396
CTTACCTAC   TCTAAATATT  AATATCACTC  TCACTAGTTG  TTTCCTCTAT  ATATACTCTT    1456
CATTTCCTTT  TCTTTTTCTT  TTTTTTTTT   TTTGTCCTGC  GTGACGATTT  CAAGCATTTC    1516
ATATAAACAC  CCACGTGATC  TAACGATAAT  TAAAACCACG  TTAATCACTA  AAAAAACTAA    1576
GAATAAAAGA  AATGGTGTTT  ATATTAGTAT  TTAGAATCTT  GATGAGTTGC  TATACCGGCG    1636
CACAGTAGGA  GGTGGTACAC  CAGCAGTAAT  AAAAATAACC  CAGGAAACAA  GAAGTAGCAG    1696
TATTATGGGA  TAAATTTAAC  AAAAATGCTG  AAAAAAAGAG  TTATTGAGA   ATGTATAATT    1756
TTTTTTTAAA  TTTATTGATT  TACATTGTTT  ACGAAGAAAG  AATAACGTGT  CGTACGAGGT    1816
GTATTTCAT   TGATGTGGCA  ATGAAAATGC  GCCGGTAGGA  CCCATTTTTA  CTTTGCTAAA    1876
ATTTATTTT   TTCTTTTTTT  TTCTTGCAAT  TTGAAATTAG  AAGTTTGAAC  ATTTATTTTC    1936
ATTCTTGTTT  GAGATAGACA  CTGTTATAGT  TTTAAGGAAT  GTTTGAATTT  ATGGTGGTGT    1996
CGTGGAGTTA  GGTGACCCTC  AAATTTCATT  GTCATGTGAG  TATGGCGCCA  TCACCCGAGA    2056
AGCCAGATCG  CATTGCAACT  CATGGTCCCA  GTAAGGGTGA  TTATACGGTC  TGAAATTGAA    2116
GTGTAACTAG  AGCTTCAAGT  TTACAAAATG  TTACGCTATC  AAAGGACGGA  GTATGATTGG    2176
AGCTGTAATT  TACAATGGTT  ATACGGGCAC  GACAAAAAAC  TTTTTTCATT  AGAAAATGAT    2236
GCTTTATAAA  ACTCATACAC  AAGTACGAGG  AAGAAAAAT   GGCAATGGTA  TCTCAGTATA    2296
ATTAAGTAAA  TTTTTTTATC  CATCTCCACC  AAAGACAGTG  ACACCGTTAC  TATTACCTAT    2356
GATAGAATTG  GGATGTAATA  GGTTTTAGTA  ACAGGGTCAT  TGCCTTTGCT  GGAAAAGGAT    2416
AAAATGAATT  ACTTGATTAT  ACTGGAAGAC  CCCTGTGATT  TTCTCCCTCG  TACTTGTATA    2476
TGGATTTTAT  AAAGTATGCT  CTTCCAATGA  GGAAAAACTA  GTTCTTGTGC  TTGCATCACC    2536
GTCGTCAACT  ACAGTCCCGG  TTTTGCTCCA  TCCTTTTAAT  AGCATAACCT  TTGTAAACTT    2596
GAAGCCTTAT  TTACACCGTC  AACTTGGACC  TCGAGGGGGG  GCCCGGTACC                2646
```

( 2 ) INFORMATION FOR SEQ ID NO:6:

( i ) SEQUENCE CHARACTERISTICS:
( A ) LENGTH: 120 amino acids (B) TYPE: amino acid
        (D) TOPOLOGY: linear (ii) MOLECULE TYPE: protein (xi) SEQUENCE DESCRIPTION: SEQ ID NO:6:

```
Met Ala Ser Ser Met Ser Leu Lys Leu Thr Cys Val Val Val Phe Cys
 1               5                  10                      15

Met Val Val Gly Ala Pro Leu Ala Gln Gly Ala Ile Ser Cys Gly Gln
            20                  25                  30

Ile Thr Ser Ala Leu Ala Pro Cys Ile Ala Tyr Leu Lys Gly Asn Gly
        35                  40                  45

Ala Gly Ser Ala Pro Pro Ala Cys Cys Asn Gly Ile Arg Ser Leu Asn
    50                  55                  60

Ser Ala Ala Lys Thr Thr Pro Asp Arg Gln Arg Ala Cys Ser Cys Ile
65                  70                  75                  80

Lys Ser Ala Ala Thr Gly Ile Ser Gly Ile Asn Tyr Ser Thr Ala Ala
                85                  90                  95

Gly Leu Pro Gly Lys Cys Gly Ile Asn Ile Pro Tyr Lys Ile Ser Pro
            100                 105                 110

Ser Thr Asp Cys Lys Ser Ile Lys
            115                 120
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Leu Pro Gly Lys Cys Gly Val Asn Ile Pro Tyr
 1               5                  10
```